US00PP35824P2

(12) United States Plant Patent
Suzuki

(10) Patent No.: US PP35,824 P2
(45) Date of Patent: May 21, 2024

(54) ***TORENIA* PLANT NAMED '17TOR1-7-04'**

(50) Latin Name: *Torenia hybrida*
Varietal Denomination: 17TOR1-7-04

(71) Applicant: Yoichi Suzuki, Aichi (JP)

(72) Inventor: Yoichi Suzuki, Aichi (JP)

(73) Assignee: HAKUSAN, Co, Ltd., Aichi (JP)

( * ) Notice: Subject to any disclaimer, the term of this patent is extended or adjusted under 35 U.S.C. 154(b) by 0 days.

(21) Appl. No.: 18/376,254

(22) Filed: Oct. 3, 2023

(51) Int. Cl.
*A01H 5/02* (2018.01)
*A01H 6/00* (2018.01)

(52) U.S. Cl.
USPC ..... Plt./487
CPC ..... *A01H 6/00* (2018.05)

(58) Field of Classification Search
USPC ..... Plt./487
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Torenia* plant named '17TOR1-7-04', characterized by its compact, semi-upright, mounding to trailing and decumbent plant habit; vigorous growth habit; freely branching habit; relatively short internodes; freely flowering habit; large reddish purple and light purple-colored flowers; and good garden performance.

2 Drawing Sheets

Figure 1:
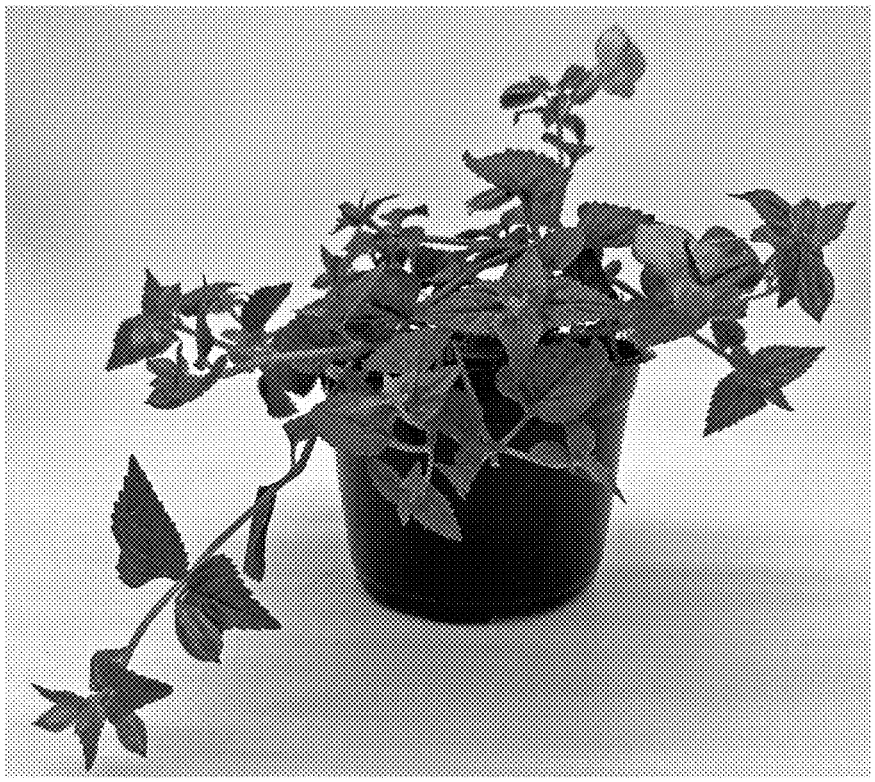

Botanical designation: *Torenia hybrida.*
Cultivar denomination: '17TOR1-7-04'.

BACKGROUND OF THE INVENTION

The present invention relates to a new and distinct cultivar of *Torenia* plant, botanically known as *Torenia hybrida*, commonly referred to as Wishbone Flower and hereinafter referred to by the name '17TOR1-7-04'.

The new *Torenia* plant is a product of a planned breeding program conducted by the Inventor in Toyota, Aichi, Japan. The objective of the breeding program is to develop new vigorous and freely branching *Torenia* plants with numerous large attractive flowers.

The new *Torenia* plant originated from a cross-pollination in Toyota, Aichi, Japan in July, 2017 of *Torenia hybrida* 'Catalina Blue River', not patented, as the female, or seed parent with *Torenia hybrida* 'Kauai Lemon Drop', not patented, as the male, or pollen, parent. The new *Torenia* plant was discovered and selected by the Inventor as a single flowering plant from within the progeny of the stated cross-pollination in a controlled greenhouse environment in Toyota, Aichi, Japan in June, 2018.

Asexual reproduction of the new *Torenia* plant by vegetative cuttings in a controlled greenhouse environment in Toyota, Aichi, Japan since July, 2017 has shown that the unique features of this new *Torenia* plant are stable and reproduced true to type in successive generations.

SUMMARY OF THE INVENTION

Plants of the new *Torenia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of '17TOR1-7-04'. These characteristics in combination distinguish '17TOR1-7-04' as a new and distinct *Torenia* plant:

1. Compact, semi-upright, mounding to trailing and decumbent plant habit.
2. Vigorous growth habit.
3. Freely branching habit.
4. Relatively short internodes.
5. Freely flowering habit.
6. Large reddish purple and light purple-colored flowers.
7. Good garden performance.

Plants of the new *Torenia* differ primarily from plants of the female parent, 'Catalina Blue River' in flower color as plants of the new *Torenia* plant have reddish purple and light purple-colored flowers whereas plants of 'Catalina Blue River' have light purple-colored flowers. In addition, plants of the new *Torenia* have larger flowers than plants of 'Catalina Blue River'.

Plants of the new *Torenia* differ primarily from plants of the male parent, 'Kauai Lemon Drop' in flower color as plants of the new *Torenia* plant have reddish purple and light purple-colored flowers whereas plants of 'Kauai Lemon Drop' have white and yellow-colored flowers. In addition, plants of the new *Torenia* are more freely branching and more high temperature-tolerant than plants of 'Kauai Lemon Drop'.

Plants of the new *Torenia* can be compared to plants of *Torenia* 'Catalina Pink', not patented. In side-by-side comparisons, plants of the new *Torenia* and 'Catalina Pink' differ primarily in flower color as plants of the new *Torenia* plant have reddish purple and light purple-colored flowers whereas plants of 'Catalina Pink' have solid pink-colored flowers. In addition, plants of the new *Torenia* are more vigorous than plants of 'Catalina Pink' .

BRIEF DESCRIPTION OF THE PHOTOGRAPHS

The accompanying colored photographs illustrate the overall appearance of the new *Torenia* plant showing the colors as true as it is reasonably possible to obtain in colored reproductions of this type. Colors in the photographs may differ slightly from the color values cited in the detailed botanical description which accurately describe the colors of the new *Torenia* plant.

The photograph on the first sheet (FIG. 1) is a side perspective view of a typical flowering plant of '17TOR1-7-04' grown in a container.

Figure 2:
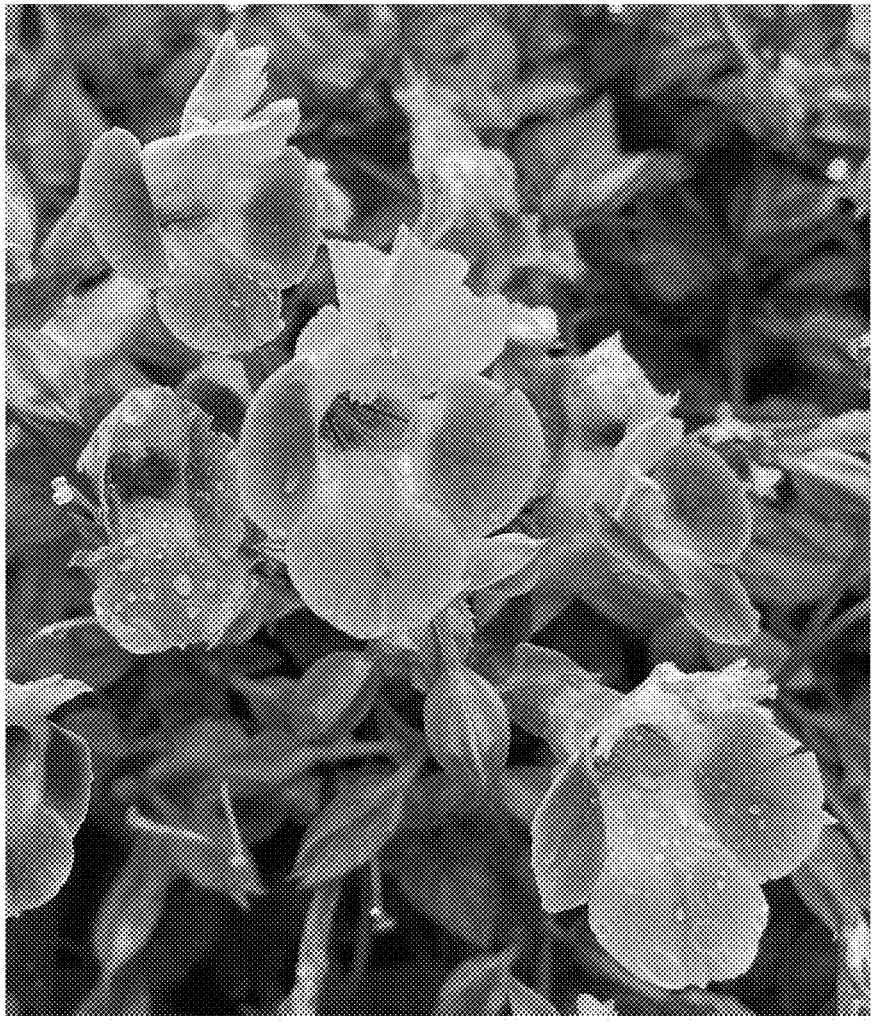

The photograph on the second sheet (FIG. 2) is a close-up view of a typical flowering plant of '17TOR1-7-04'.

DETAILED BOTANICAL DESCRIPTION

The aforementioned photographs and following observations and measurements describe plants grown during the late spring in 10-cm containers in a glass-covered greenhouse in Loudon, New Hampshire and under cultural practices typical of commercial *Torenia* production. During the production of the plants, day and night temperatures averaged 20° C. Plants were seven and nine weeks from planting rooted cuttings when the photographs and description, respectively, were taken. In the following description, color references are made to The Royal Horticultural Society Colour Chart, 2015 Edition, except where general terms of ordinary dictionary significance are used.

Botanical classification: *Torenia hybrida* '17TOR1-7-04'.

Parentage:

*Female, or seed, parent.*—*Torenia hybrida* 'Catalina Blue River', not patented.

*Male, or pollen, parent.*—*Torenia hybrida* 'Kauai Lemon Drop', not patented.

Propagation:

*Type.*—By vegetative terminal cuttings.

*Time to initiate roots.*—About two weeks at ambient temperatures about 30° C.

*Time to produce a rooted young plant roots.*—About four weeks at ambient temperatures about 15° C.

*Root description.*—Fibrous; medium in thickness; typically creamy white in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Compact, semi-upright, mounding to trailing and decumbent plant habit; vigorous growth habit; freely branching habit with lateral branches potentially developing at every node, pinching enhances branching potential.

*Plant height.*—About 11 cm.

*Plant width (spread).*—About 37.5 cm.

*Lateral branches.*—Length: About 15 cm. Diameter: About 2 mm. Internode length: About 2.1 cm. Aspect: Upright to outwardly spreading. Texture and luster: Smooth, glabrous; matte to slightly glossy. Color: Close to 144A to 144B.

Leaf description:

*Arrangement.*—Opposite, simple.

*Length.*—About 2.9 cm.

*Width.*—About 2.4 cm.

*Shape.*—Ovate.

*Apex.*—Acute.

*Base.*—Cordate to truncate.

*Margin.*—Dentate to serrate.

*Texture and luster, upper surface.*—Smooth, glabrous; slightly glossy.

*Texture and luster, lower surface.*—Smooth, glabrous; matte.

*Venation pattern.*—Pinnate; reticulate.

*Color.*—Developing leaves, upper surface: Close to 137B to 137C. Developing leaves, lower surface: Close to 146B. Fully expanded leaves, upper surface: Close to 146A; venation, close to 146B. Fully expanded leaves, lower surface: Close to 147B; venation, close to 145A.

*Petioles.*—Length: About 6 mm. Diameter: About 2 mm. Texture and luster, upper and lower surfaces: Smooth, glabrous; slightly glossy to matte. Color, upper surface: Close to 146B to 146C. Color, lower surface: Close to 144B.

Flower description:

*Flower form and flowering habit.*—Single flowers borne in upper leaf axils or terminally; corolla bilabiate and calyx tubular; flowers face upright to outwardly; freely flowering habit with about 52 flower buds and open flowers per plant at one time.

*Fragrance.*—None detected.

*Natural flowering season.*—Plants begin flowering about three to four weeks after planting rooted cuttings; long flowering period; continuously flowering from early summer to late autumn in Japan.

*Postproduction longevity.*—Depending on temperature, flowers last about four days on the plant; flowers persistent.

*Flower buds.*—Height: About 1.75 cm. Diameter: About 5 mm. Shape: Ellipsoidal. Color: Close to 144A.

*Flower diameter.*—About 2 cm by 2.4 cm.

*Flower depth.*—About 3.4 cm.

*Throat diameter.*—About 5 mm by 6 mm.

*Tube diameter, base.*—About 2 mm.

*Tube length.*—About 2 cm.

*Petals.*—Quantity per flower: Bilabiate with one upper or banner petal with two fused lobes and one lower petal with two lateral lobes and a single lower lobe, petals fused. Upper petal, fused lobes: Length: About 1.1 cm. Width: About 1.5 cm. Shape: Roughly spatulate. Apex: Obtuse to cordate. Margin: Entire; slightly undulate. Texture and luster, upper and lower surfaces: Smooth, glabrous; velvety; matte to slightly glossy. Color: Developing, upper and lower surfaces: Close to N75A to N75B. Fully developed, upper and lower surfaces: Close to 76B to 76C. Lower petal, lateral and lower lobes: Length: About 1 cm. Width: About 1.1 cm. Shape: Roughly spatulate. Apex: Obtuse. Margin: Entire; slightly undulate. Texture and luster, upper surface: Smooth, glabrous; velvety; matte to slightly glossy. Texture and luster, lower surface: Smooth, glabrous; velvety; matte. Color: Developing, upper surface: Close to 71A. Developing, lower surface: Close to 72B. Fully developed, upper surface: Close to 71A to 71B. Fully developed, lower surface: Close to 72B. Throat texture and luster: Smooth, glabrous; matte to slightly glossy. Throat color: Distally, close to 76B to 76C; proximally, close to 5A with stripes, close to 72A. Tube texture and luster: Smooth, glabrous; slightly glossy. Tube color: Close to 75A.

*Sepals*.—Quantity per flower: Typically five, fused. Length: About 1.7 cm. Width: About 3 mm. Shape: Lanceolate to linear. Apex: Acuminate. Margin: Entire. Texture and luster, upper and lower surfaces: Smooth, glabrous; slightly glossy. Color, upper and lower surfaces: Close to 144A to 144B.

*Peduncles*.—Length: About 1.1 cm. Diameter: About 1.5 mm. Aspect: Upright to slightly outwardly. Texture and luster: Smooth, glabrous; slightly glossy. Color: Close to 144A.

*Reproductive organs*.—Stamens: Quantity per flower: Typically four; two pairs of fused anthers. Filament length: About 2.1 mm to 2.9 mm. Anther shape: Ellipsoidal. Anther size: About 1.25 mm by 4 mm. Anther color: Close to NN155C to NN155D. Pollen amount: None observed. Pistils: Quantity per flower: One. Pistil length: About 2.3 cm. Stigma shape: Trullate. Stigma color: Close to NN155D. Style color: Close to NN155D. Ovary color: Close to 144A.

*Seeds and fruits*.—To date, seed and fruit development have not been observed on plants of the new *Torenia*.

Pathogen & pest resistance: Plants of the new *Torenia* have been observed to be resistant to Powdery Mildew. To date, plants of the new *Torenia* have not been noted to be resistant to pests and other pathogens common to *Torenia* plants.

Garden performance: Plants of the new *Torenia* have been observed to have good garden performance and to tolerate rain, wind and temperatures ranging from about 5° C. to about 35° C.

It is claimed:

1. A new and distinct *Torenia* plant named '17TOR1-7-04' as illustrated and described.

* * * * *